United States Patent
Jain et al.

(10) Patent No.: US 11,147,532 B2
(45) Date of Patent: Oct. 19, 2021

(54) THREE-DIMENSIONAL NEEDLE LOCALIZATION WITH A TWO-DIMENSIONAL IMAGING PROBE

(75) Inventors: Ameet Kumar Jain, Eindhoven (NL); Francois Guy Gerard Marie Vignon, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 984 days.

(21) Appl. No.: 14/118,244

(22) PCT Filed: Jun. 6, 2012

(86) PCT No.: PCT/IB2012/052830
§ 371 (c)(1),
(2), (4) Date: Nov. 18, 2013

(87) PCT Pub. No.: WO2012/172458
PCT Pub. Date: Dec. 20, 2012

(65) Prior Publication Data
US 2014/0094695 A1    Apr. 3, 2014

Related U.S. Application Data

(60) Provisional application No. 61/496,077, filed on Jun. 13, 2011.

(51) Int. Cl.
*A61B 8/08* (2006.01)
*A61B 8/00* (2006.01)
(Continued)

(52) U.S. Cl.
CPC .......... *A61B 8/0841* (2013.01); *A61B 8/4483* (2013.01); *A61B 8/467* (2013.01);
(Continued)

(58) Field of Classification Search
None
See application file for complete search history.

(56) References Cited

U.S. PATENT DOCUMENTS 5,830,145 A  11/1998  Tenhoff
6,038,468 A   3/2000  Rex
(Continued)

FOREIGN PATENT DOCUMENTS

EP    1245191 A2   10/2002
JP    H10277040 A  10/1998
(Continued)

OTHER PUBLICATIONS

U.S. Appl. No. 61/375,093, filed Aug. 19, 2010 (37 pages, including drawings).*
(Continued)

*Primary Examiner* — Bill Thomson
*Assistant Examiner* — Helene Bor

(57) ABSTRACT

An imaging system and method include a medical device (102) having a tracking element (106) mounted thereon. An array (109) of transducers is spaced apart from one another for exchanging energy in a subject between tracking element and the array of transducers. A trilateration module (104) is configured to interpret signals sensed between tracking element and the array of transducers to compute times of flight of signals associated with the transducers in the array such that a position of tracking element is determined in at least two dimensions to locate a position of the medical device in a visual image.

18 Claims, 6 Drawing Sheets

(51) Int. Cl.
   *A61B 34/20*        (2016.01)
   *A61B 90/00*        (2016.01)
(52) U.S. Cl.
   CPC .............. *A61B 8/481* (2013.01); *A61B 8/52* (2013.01); *A61B 34/20* (2016.02); *A61B 8/4494* (2013.01); *A61B 8/461* (2013.01); *A61B 8/466* (2013.01); *A61B 8/5261* (2013.01); *A61B 2034/2051* (2016.02); *A61B 2034/2063* (2016.02); *A61B 2090/3929* (2016.02)

(56) References Cited

U.S. PATENT DOCUMENTS

| | | | |
|---|---|---|---|
| 6,120,453 A * | 9/2000 | Sharp | A61B 8/15 |
| | | | 128/916 |
| 6,216,540 B1 * | 4/2001 | Nelson et al. | 73/633 |
| 6,246,898 B1 * | 6/2001 | Vesely | A61B 5/0422 |
| | | | 600/424 |
| 6,298,261 B1 * | 10/2001 | Rex | A61B 5/06 |
| | | | 600/424 |
| 6,587,709 B2 * | 7/2003 | Solf et al. | 600/424 |
| 6,592,520 B1 * | 7/2003 | Peszynski et al. | 600/437 |
| 7,052,461 B2 | 5/2006 | Willis | |
| 8,317,712 B2 | 11/2012 | Burcher et al. | |
| 8,429,972 B2 | 4/2013 | Karasawa | |
| 8,956,297 B2 | 2/2015 | Sumi | |
| 9,282,946 B2 * | 3/2016 | Vignon | A61B 34/20 |
| 2003/0060700 A1 | 3/2003 | Solf et al. | |
| 2005/0033165 A1 * | 2/2005 | Ustuner | A61B 8/5269 |
| | | | 600/437 |
| 2005/0062469 A1 * | 3/2005 | Anderson | A61B 34/20 |
| | | | 324/207.17 |
| 2007/0161905 A1 | 7/2007 | Munrow | |
| 2007/0167823 A1 | 7/2007 | Lee et al. | |
| 2007/0213616 A1 * | 9/2007 | Anderson | A61B 50/13 |
| | | | 600/448 |
| 2008/0161684 A1 * | 7/2008 | Li | A61B 5/06 |
| | | | 600/426 |
| 2009/0292209 A1 | 11/2009 | Hadjicostis | |
| 2010/0210943 A1 * | 8/2010 | Mahmoud | A61B 8/14 |
| | | | 600/437 |
| 2011/0112403 A1 * | 5/2011 | Machtey et al. | 600/443 |
| 2012/0197108 A1 * | 8/2012 | Hartmann | A61B 6/4405 |
| | | | 600/424 |
| 2013/0204138 A1 * | 8/2013 | Belohlavek | A61B 34/20 |
| | | | 600/453 |
| 2013/0217997 A1 * | 8/2013 | Byrd | A61B 5/06 |
| | | | 600/409 |
| 2013/0245433 A1 * | 9/2013 | Deladi | A61B 8/0883 |
| | | | 600/424 |
| 2014/0316269 A1 * | 10/2014 | Zhang | A61B 8/4494 |
| | | | 600/439 |
| 2014/0364734 A1 * | 12/2014 | Huang | 600/447 |
| 2016/0045184 A1 * | 2/2016 | Courtney | A61B 8/4245 |
| | | | 600/424 |

FOREIGN PATENT DOCUMENTS

| | | |
|---|---|---|
| JP | 2003101861 A | 4/2003 |
| WO | 2010004564 A2 | 1/2010 |

OTHER PUBLICATIONS

F. Ahmad and M. G. Amin, "Noncoherent approach to through-the-wall radar localization," in IEEE Transactions on Aerospace and Electronic Systems, vol. 42, No. 4, pp. 1405-1419, Oct. 2006, doi: 10.1109/TAES.2006.314581. (Year: 2006).*

True range multilateration. (Jul. 1, 2005). Retrieved May 11, 2020, from https://en.wikipedia.org/w/index.php?title=True_range_multilateration&oldid=17932202 (Year: 2005).*

"Time of Flight and FMCW Catheter Localization" Mung et al, Ultrasonics Symposium 2009 IEEE, Sep. 20, 2009 p. 590-593.

* cited by examiner

THREE-DIMENSIONAL NEEDLE LOCALIZATION WITH A TWO-DIMENSIONAL IMAGING PROBE

CROSS-REFERENCE TO PRIOR APPLICATIONS

This application is the U.S. National Phase application under 35 U.S.C. § 371 of International Application Serial No. PCT/IB2012/052830, filed on Jun. 6, 2012, which claims the benefit of U.S. Application Ser. No. 61/496,077, filed on Jun. 13, 2011. These applications are hereby incorporated by reference herein.

This disclosure relates to medical devices and procedures, and more particularly to systems and methods for medical device localization in three dimensions using one or two-dimensional imaging probes.

Needle insertion under ultrasound guidance is commonly performed, e.g., for biopsies, fluid drainage, nerve blocks, vascular access, etc. Needle visualization techniques have been successfully implemented based on steering imaging beams approximately perpendicular to the needle shaft (using, e.g., needle visualization enhancement software).

In a significant number of cases, the needle deviates from the imaging plane due to tissue heterogeneities and bevel asymmetry. An out-of-plane needle disappears no matter how smart needle visualization enhancement software is, because the needle receives no ultrasound energy at all. A clinician then has to move the imaging transducer to find the needle and usually loses an original target plane. Furthermore, the clinician does not know where the needle is in relation to the imaging plane and therefore has no indication of how to move the transducer to find the needle.

In accordance with the present principles, an imaging system and method include a medical device having a tracking element mounted thereon. An array of transducers has the transducers spaced apart from one another for exchanging energy in a subject between the tracking element and the array of transducers. A trilateration module is configured to interpret signals sensed between tracking element and the array of transducers to compute times of flight of signals associated with the transducers in the array such that a position of tracking element is determined in at least two dimensions to locate a position of the medical device in a visual image.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
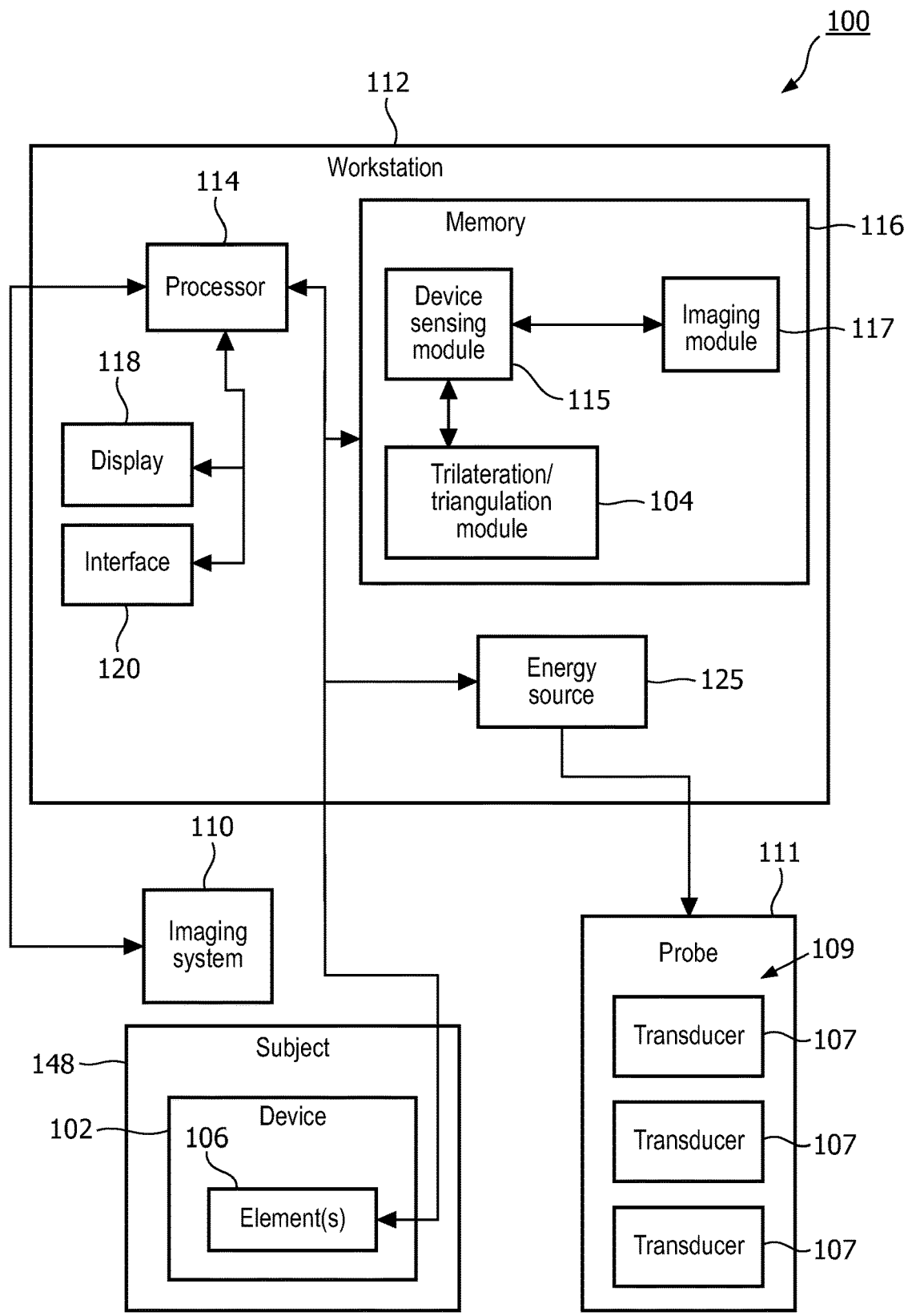
FIG. 1 is a block/flow diagram showing a system/method for imaging a medical device in accordance with one illustrative embodiment.

In accordance with the present principles, a target plane, a relative position and trajectory of a medical device (e.g., with respect to a target anatomy of the target plane) need to be imaged at the same time to avoid issues related to losing an out-of-plane needle image during a procedure. One-dimensional (1D) ultrasound probes are used for two-dimensional (2D) visualization of needles with respect to the anatomy in a wide range of clinical interventions. However the position of the needle or tool cannot be assessed when the needle or tool lies outside of the imaging plane. The present systems and methods are provided for tracking and visualizing out-of-plane needles without losing the target anatomy image. In one embodiment, this is achieved using a simple one-dimensional (1D) probe (for 2D imaging) or using a two-dimensional (2D) probe for 3D imaging. Methods for assessing the 3D position of a needle with respect to the imaging plane using a 1D array are also provided.

An ultrasound element (passive or active) is embedded in a tracked tool, e.g., at a tip of the tool. Ultrasound signal times-of-flight between the tracked element and multiple elements of the imaging probe are used in a three-dimensional (3D) triangulation or trilateration routine to yield the position of the tracked element. As a result, ultrasound-guided needle interventions are greatly facilitated, without the need for expensive additional equipment (e.g., matrix arrays).

It also should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a system 100 for performing a medical procedure is illustratively depicted. System 100 may include a workstation or console 112 from which a procedure is supervised and managed. Procedures may include any procedure including but not limited to biopsies, ablations, injection of medications etc. Workstation 112 preferably includes one or more processors 114 and memory 116 for storing programs and applications. It should be understood that the function and components of system 100 may be integrated into one or more workstations or systems.

Memory 116 may store a device sensing module 115 configured to interpret electromagnetic, optical and/or acoustic feedback signals from a medical device 102. The sensing module 115 is configured to use the signal feedback (and any other feedback) to provide a location or to depict the medical device 102 in medical images. The medical device 102 may include, e.g., a needle, a catheter, a guide wire, an endoscope, a probe, a robot, an electrode, a filter device, a balloon device or other medical component, etc. Workstation 112 may include a display 118 for viewing internal images of a subject using an imaging system 110. The imaging system 110 may include imaging modalities such as ultrasound, fluoroscopy, photoacoustics, etc. The imaging system 110 may also include, e.g., a magnetic resonance imaging (MRI) system, a fluoroscopy system, a computed tomography (CT) system, an ultrasound system or other system. Display 118 may also permit a user to interact with the workstation 112 and its components and functions. This is further facilitated by an interface 120 which may include a keyboard, mouse, a joystick or any other peripheral or control to permit user interaction with the workstation 112.

One or more sensors/transducers 106 may be incorporated into the device(s) 102, so tracking information from an energy source 125 can be detected at the device(s) 102.

It should be understood that while the present illustrative example will be described in terms of a tracked element 106 (on the device 102) being a receiver while tracking elements or transducers 107 (of an imaging array 109) are transmitters, the opposite configuration may also be provided. For example, the same times-of-flight may be measured by using the tracked element 106 (on the device 102) as a transmitter, and the tracking elements/transducers 107 (of the array 109) may act as receivers.

The energy source 125 need not be provided from a source external to a body/subject 148, and may be from an internal source or from another imaging device 110. In one embodiment, the energy source is an ultrasonic source. The sensors/elements 106 may be employed to detect electromagnetic energy or acoustic energy (or transmit the energy). This permits the exchange of energy which will be used to interpret a position and/or orientation of the device 102. The signals will be employed as feedback to make adjustments or otherwise perform the medical procedure. The transducers 107 may include an ultrasonic sensor or sensors (disposed in a probe) or other sensor or transmission devices.

Imaging system 110 may be provided to collect real-time intra-operative imaging data. The imaging data may be displayed on display 118. Sensing module 115 may determine positions of the sensors/elements 106 and therefore the device 102 within the real-time images based upon energy measured by the sensors/elements 106. This may include employing a trilateration or triangulation method/module 104 as will be described herein. A digital rendering of the medical device 102 (using feedback signals) can be displayed to realize the position of the device 102 against the real-time images (tracking). The digital rendering may be generated by an image processing module 117.

It should be understood that tracking and imaging using an ultrasonic system may occur concurrently or sequentially. In preferred embodiments, an imaging array of transducers is the same as the tracking array of transducers. It is possible to use the imaging beams to track and vice versa (use the tracking beams to image). However, the tracking beams as described herein may not be suitable for ultrasound imaging. In such cases, imaging frames and tracking frames may be interleaved (alternated). If the tracked element is a transmitter, then either its bandwidth needs to be separate from that of the imaging pulses, or scanning may be interrupted during reception of the signals from the tracked element. Other techniques may also be employed to ensure both operations (e.g., tracking and imaging) are performed in real-time.

In one embodiment, the imaging system 110 includes an ultrasonic system, and the emissions are acoustic in nature. In this case, the sensor(s) 106 include ultrasonic sensors which detect acoustic signals generated by ultrasonic transducers 107 arranged in an array 109 on an ultrasonic probe 111. In this way, both anatomical images and device images can concurrently be displayed.

In another useful embodiment, an interventional application includes the use of two or more medical devices inside of a subject 148. For example, one device 102 may include a guide catheter, which is placed at one point, and another device 102 may include a needle for performing an ablation or biopsy at fixed/different points along the length of the catheter. Other combinations of devices are also contemplated.

In accordance with one particularly useful embodiment, one or several ultrasound sensors 106 are mounted on a tracked tool or device 102. The tool 102 is tracked using the sensor 106 for tracking the position of the device 102. A 1D imaging array 109 is provided for imaging the tool 102 in accordance with the sensors 106. The array 109 may include a line of transducers (receivers or transmitters) 107 to form the 1D dimensional array 109. The one dimensional array may include a straight arrangement (line) of transducers 107 or may include transducers 107 disposed on a curved path (arc).

In one embodiment, a physically planar array may be employed using beamforming techniques to spatially shift an origin of a time-of-flight sphere emanating from the physical array elements 107. By focusing several physical elements into one location in space (using appropriate time delays) the focus location becomes a virtual element.

The sensing module 115 includes a three-dimensional (3D) trilateration routine that tracks the ultrasound elements 106 aboard the tool 102. In one embodiment, the display 118 provides a 3D rendering of the tracked tool 102 superimposed on a 2D ultrasound image. The position of the tool 102 will be determined as illustratively described with reference to FIGS. 2A-2B.

Figure 2B:
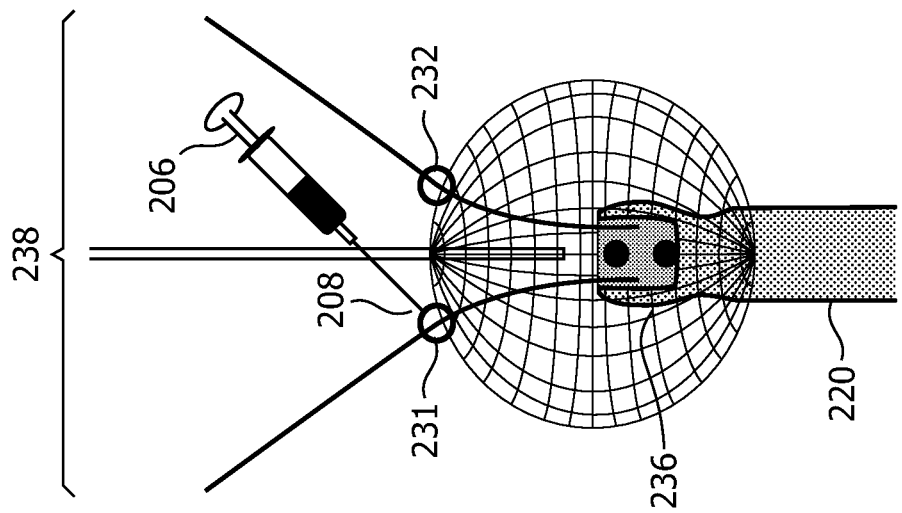
FIG. 2B is a diagram showing a front-view of the time-of-flight spheres emanating from array elements of the probe and showing true and symmetric intersection points in accordance with one illustrative embodiment.
Figure 2A:
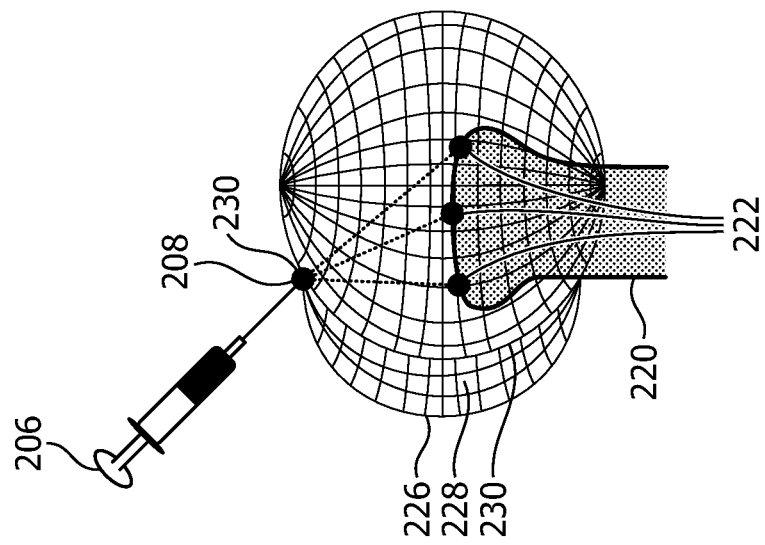
FIG. 2A is a diagram showing a side-view of time-of-flight spheres emanating from transducer array elements of a probe in accordance with one illustrative embodiment.

Referring to FIGS. 2A and 2B, diagrams show a tracked tool 206 (e.g., a needle) having an element 208 (e.g., an ultrasonic element for transmitting or receiving) at its tip depicted in the vicinity of a curved array (2D probe or a 1D array) ultrasonic probe 220 having a plurality of ultrasound (US) transducers or elements 222 (for transmitting or receiving). In accordance with the present principles, a 3D position of the tool 206 with respect to an imaging plane is assessed using the 1D array of transducers 222 in the probe 220. The ultrasound element 208 (passive or active) is embedded in the tracked tool 206, for example, at its tip. Ultrasound signal times-of-flight between the tracked element 208 and the multiple transducers 222 of the imaging probe 220 are used in a 3D triangulation or trilateration routine (104 in FIG. 1) to yield the position of the tracked element 208. It should be understood that a plurality of elements 208 may be employed on the tool 206. Each sensor's position may be tracked using the present principles to describe its position during a procedure.

Time-of-flight trilateration of ultrasound signals between the tracked element 208 and several transducers 222 of the imaging array can yield 3D positioning as long as the imaging array transducers 222 used are not collinear relative to the element 208. The position of the tracked element 208 is at an intersection of at least three spheres 226, 228, 230 centered on the tracking transducers 222 (of the array) and with radii determined by a measured time of flight between the tracked element 208 and the tracking transducers 222. The intersection of three spheres 226, 228, 230 results in two points (e.g., true intersection 231 and a symmetric intersection 232) as long as the three spheres' centers are not collinear with respect to the tracked element 208 (the intersection of two spheres are a circle, the intersection of the last sphere with the circle yields two points).

Trilateration is employed to determine the position of the tracked element 208 and therefore the needle or tool 206. Trilateration is the process of determining absolute or relative locations of points by measurement of distances, using the geometry of spheres or triangles. In contrast to triangulation, it does not involve the measurement of angles although triangulation techniques may also be employed.

In two-dimensional space, using two reference points is normally sufficient to leave only two possibilities for the location determined, and the tie is broken by including a third reference point or other information. In three-dimensional space, using three reference points similarly leaves only two possibilities, and the tie is broken by including a fourth reference point or other information.

Figure 3:
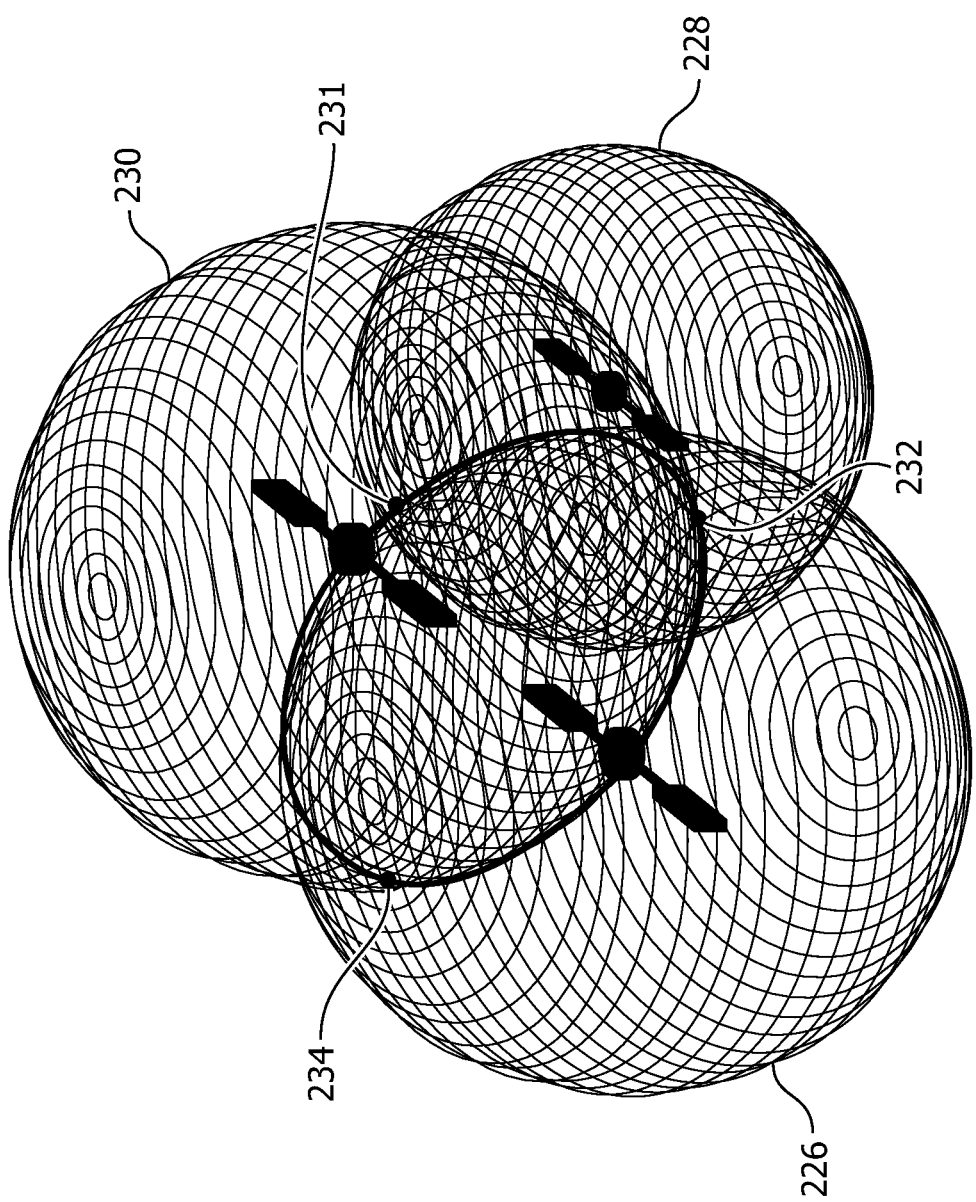
FIG. 3 is a perspective view showing three spheres intersecting to demonstrate trilateration in accordance with the present principles.

Referring to FIG. 3, a solution is found by formulating equations for the three sphere surfaces 226, 228 and 230 and then solving the three equations for the three unknowns, x, y, and z. The equations for the three spheres may be expressed as:

$$r_1^2 = x^2 + y^2 + z^2$$

$$r_2^2 = (x-d)^2 + y^2 + z^2$$

$$r_3^2 = (x-i)^2 + (y-j)^2 + z^2$$

We need to find a point located at (x, y, z) that satisfies all three equations.

First, we subtract the second equation from the first and solve for x:

$$x = \frac{r_1^2 - r_2^2 + d^2}{2d}.$$

We assume that the first two spheres intersect in more than one point, that is that $d-r_1 < r_2 < d+r_1$. In this case, substituting the equation for x back into the equation for the first sphere produces the equation for a circle, the solution to the intersection of the first two spheres:

$$y^2 + z^2 = r_1^2 - \frac{(r_1^2 - r_2^2 + d^2)^2}{4d^2}.$$

Substituting $y^2 + z^2 = r_1^2 - x^2$ into the formula for the third sphere and solving for y results in the following:

$$y = \frac{r_1^2 - r_3^2 - x^2 + (x-i)^2 + j^2}{2j} = \frac{r_1^2 - r_3^2 + i^2 + j^2}{2j} - \frac{i}{j}x.$$

Now that the x- and y-coordinates of the solution point are obtained, the formula for the first sphere can be rearranged to find the z-coordinate:

$$z = \pm\sqrt{r_1^2 - x^2 - y^2}.$$

Now we have the solution for x, y and z. Because z is expressed as the positive or negative square root, it is possible for there to be zero, one or two solutions to the problem. This can be visualized as taking a circle 234 found from intersecting a first 226 and second sphere 230 and intersecting that with a third sphere 228. If that circle 234 falls entirely outside or inside of the sphere 228, z is equal to the square root of a negative number: no real solution exists. If that circle 234 touches the sphere 228 on exactly one point, z is equal to zero. If that circle 234 touches the surface of the sphere at two points, then z is equal to plus or minus the square root of a positive number (as depicted in FIG. 3).

Referring again to FIGS. 2A and 2B, it is now possible to map the 3D position of the tracked element 208 with a 1D curvilinear imaging array (222). With a linear array where elements are collinear, transmit or receive focusing can generate virtual transducers in the array that would no longer be aligned, so that the technique is also applicable to linear arrays with some beamforming. Beamforming in effect moves an origin of a sphere by moving the origin of a transmitted signal to a new location.

There may be uncertainty since the trilateration yields two positions (symmetric with respect to the imaged plane). This uncertainty can be broken using a priori knowledge, or by gently rocking the ultrasound probe 220 and observing the relative movement of the tracked element 208 (getting closer or farther relative to the target plane). Also, a single additional imaging sensor, transducer or element 236 (or transmitter) may also be employed on a side of the imaging array 222 to break the uncertainty (tie-breaker).

The present technique can detect the tracked elements 208 if the elements 208 are within a plane thickness 238, that is, near an imaging plane. Customized probe design (with little elevation focusing to generate a compromise between image quality and tracking field-of-view) may be employed to extend the functionality of the system for specific applications.

In conventional systems, if a one-dimensional (1D) ultrasound (US) probe is employed for 2D visualization of needles or other tools, the position of the tool cannot be assessed for imaging when the tool lies outside of an US imaging plane 239. Two-dimensional (2D) ultrasound probes (1D curved arrays) may be employed for 2D visualization of needles with respect to a patient's anatomy in a wide range of clinical interventions. In conventional systems, clinicians spend a considerable amount of time orienting the needle fully inside the plane to visualize the needle. From oblique/orthogonal injections, the needle is very difficult to visualize. However, in accordance with the present principles, the needle or tool can be located and imaged in three dimensions while also displaying the target area. In this way, the needle is easy to find and its position accurately tracked for any type of procedure, such as, ultrasound-guided needle interventions, e.g., nerve blocks, biopsies, vascular access, abscess drainage, ablation, etc. US-guided needle interventions are greatly facilitated, without the need for expensive additional equipment (matrix arrays). US-guided interventions become (i) more accurate; (ii) faster and (iii) inexpensive (by using 2D probes).

Figure 4:
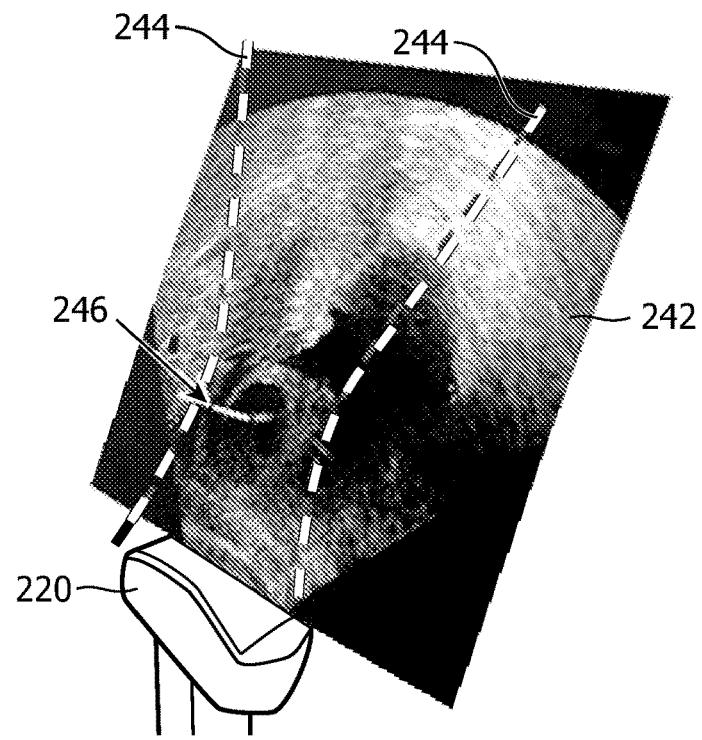
FIG. 4 is a two-dimensional ultrasound image having a three-dimensional rendering of a needle in accordance with the present principles.

Referring to FIG. 4, an illustrative two-dimensional ultrasonic image 242 is depicted showing a three-dimensional rendering of a needle 246 in accordance with one embodiment. The needle 246 is shown within image boundaries 244, but can be tracked outside of these boundaries 244. The rendering of needle 246 is generated using trilateration as described above. The needle movement is tracked and displayed along with surrounding tissues in real-time. The present principles permit fast and accurate imaging with a relatively inexpensive setup.

Figure 5A:
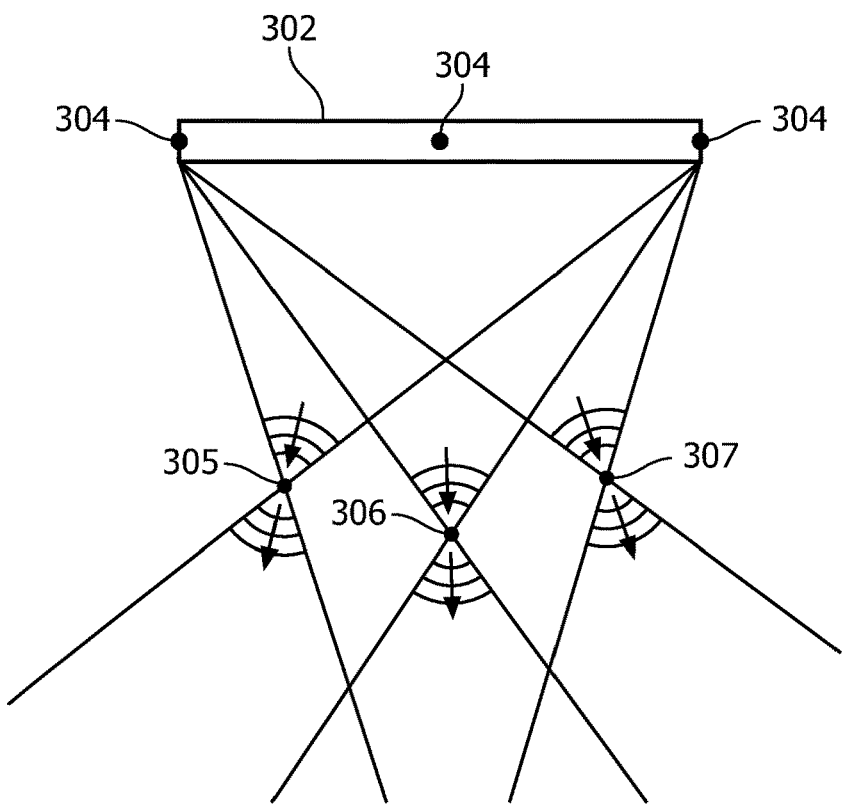
FIG. 5A is a schematic diagram showing elements of a physical array focused/beamformed to form virtual transmitter elements in accordance with one embodiment.
Figure 5B:
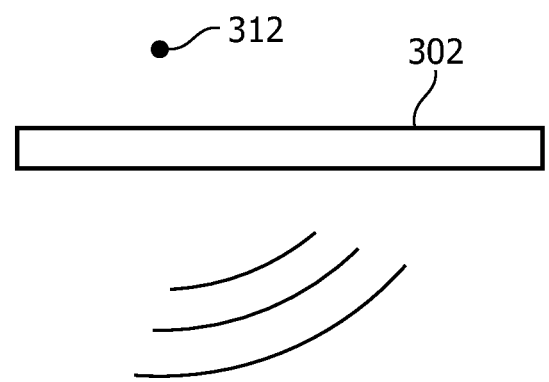
FIG. 5B is a schematic diagram showing a virtual element formed behind a physical array in accordance with another embodiment.
Figure 5C:
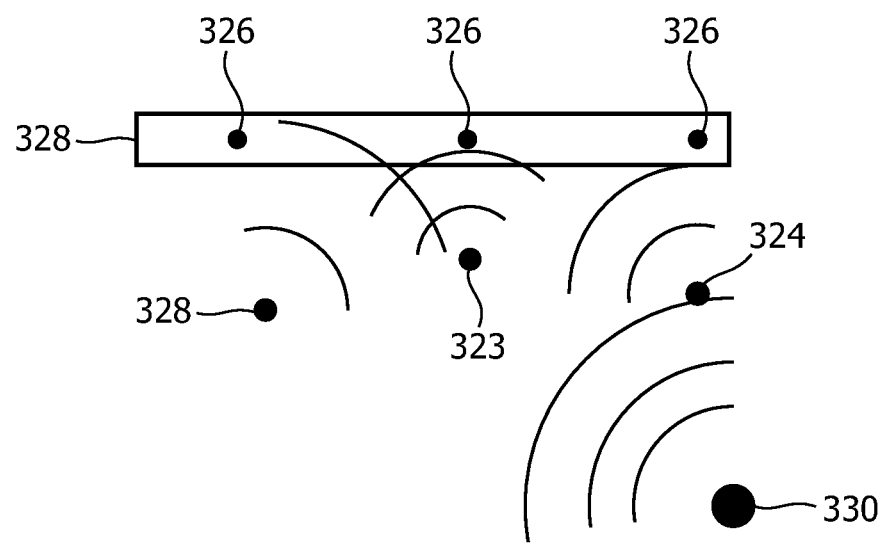
FIG. 5C is a schematic diagram showing elements of a physical array beamformed to form virtual receiver elements based on signal delays in accordance with another embodiment.

FIGS. 5A-5C will describe beamforming techniques. Beamforming can spatially shift the origin of spheres (for times of flight) from physical array elements to virtual array elements. By focusing several physical elements into one location in space (using appropriate time delays), the focus location becomes a virtual element.

Referring to FIG. 5A, a transducer array 302 includes physical elements 304, which transmit focused energy. Illustratively, beams intersect at focus locations 305, 306 and 307. These focus locations 305, 306 and 307 may be employed as sphere centers for performing time-of-flight trilateration computations. The focus locations 305, 306 and 307 advantageously provide non-collinear virtual elements which can enable the use of a planar one-dimensional transducer array configuration 302. In this configuration, a tracking sensor 310 on a medical device acts as a receiver to receive the energy from the virtual elements (305, 306 and 307) to perform position estimation as described.

Referring to FIG. 5B, virtual elements may also be projected from behind a physical array 302. For example, beamforming may be employed to project a virtual element 312 which is on an opposite side of the array 302 from that of the sensor 310 attached to the medical device.

Referring to FIG. 5C, in this embodiment, a device element 320 functions as a transmitter and virtual elements 322, 323 and 324 function as receivers. The virtual elements 322, 323 and 324 correspond with physical elements 326 in a physical array 328. The physical elements 326 receive signals transmitted from the device element 320. The signal delays measured at the physical elements 326 are transformed to enable measurements from the perspective of the virtual elements 322, 323 and 324. In so doing, beamforming is employed to eliminate collinearity between physical elements 326.

Figure 6:
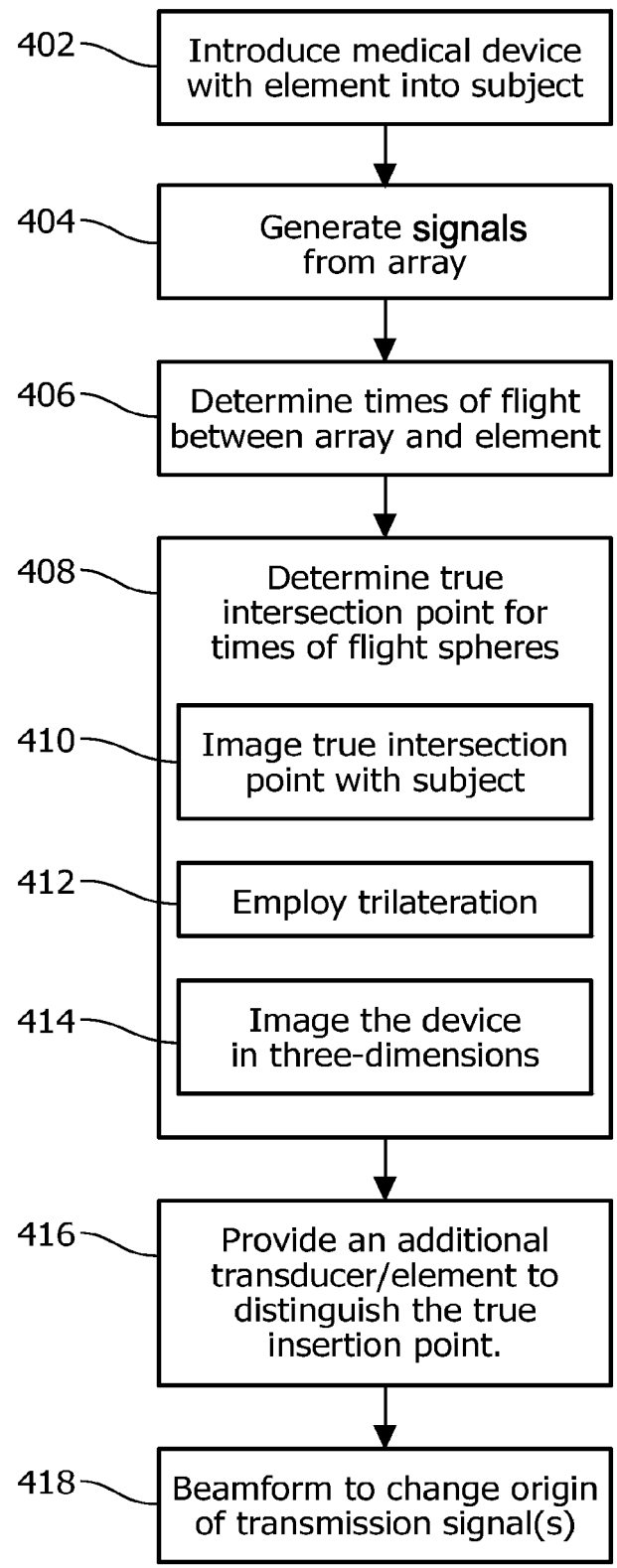
FIG. 6 is a block/flow diagram showing a system/method for imaging a medical device in accordance with another illustrative embodiment.

Referring to FIG. 6, a block/flow diagram shows a method for imaging a medical device in accordance with one illustrative embodiment. In block 402, a medical device is introduced into a subject. The medical device includes at least one element for exchanging signals. The medical device may include at least one of a needle, a catheter, a probe, a robot, a filter device, an electrode, etc.

In block 404, signals are generated by an energy source and exchanged between the at least one element on the medical device and a plurality of transducers arranged in an array. The array may be a one-dimensional array (with linear elements) or a curved or staggered array (two-dimensional). In block 406, times of flight of the signals between the transducers and the at least one element are determined. This may include measuring the time that a pulse or signal from the transducers is received at the at least one element (or vice versa).

In block 408, a true intersection point is determined for spheres having radii defined by the times of flight. In block 410, the true intersection point is imaged over time along with the subject to track a position of the medical device. The trilateration is employed to determine the true intersection point in block 412. In block 414, the array of transducers may be disposed in a one dimensional array along a line or curved surface. The imaging may include imaging the medical devices in three-dimensions using trilateration of the at least one element relative to at least three transducers.

In block 416, an additional element/transducer may be configured to distinguish between the true intersection point and a symmetric intersection point. This may include adding the transducer at a location where the true and symmetric intersections can be distinguished. Other techniques for distinguishing the intersection points may also be employed.

In block 418, the time-of-flight spheres preferably have centers that are non-collinear relative to the at least one sensor. However, in the event that the spheres are collinear, beamforming may be employed for transmitted signals from one or more transmitters to provide a new origin for the transmitted signal and eliminate the collinearity.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for systems and methods for three-dimensional needle localization with a two-dimensional imaging probe (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

Having thus described the details and particularity required by the patent laws, what is claimed and desired protected by Letters Patent is set forth in the appended claims:

1. An imaging system, comprising:
a medical device having at least one tracking element mounted thereon;
an imaging device to generate a visual image;
an array of transducers having transducer elements spaced apart from one another for exchanging energy in a subject between the at least one tracking element and the array of transducers, the array of transducers generating three virtual elements that are non-collinear with respect to the transducer elements; and
trilateration circuitry to interpret signals sensed between the at least one tracking element mounted on the medical device and inserted in the subject, and the array of transducers, to compute times of flight of signals associated with a plurality of the transducer elements in the array and perform a trilateration procedure to yield a position of the at least one tracking element within the subject by generating a plurality of virtual spheres that intersect at a true intersection point and a symmetric intersection point, and based on the times of flight of signals associated with the plurality of the transducer elements to determine a position of the at least one tracking element in at least two dimensions to locate a position of the medical device in the visual image.

2. The system as recited in claim 1, wherein the array of transducers are disposed in a one dimensional array along one of a line and an arc.

3. The system as recited in claim 1, wherein the array of transducers includes ultrasonic transducers and the at least one tracking element includes an ultrasonic transducer element.

4. The system as recited in claim 1, wherein each of said virtual spheres emanates from one transducer element of the array of transducers and has a radius defined by a time of flight of signal associated with the transducer element that the virtual sphere emanates therefrom.

5. The system as recited in claim 1, wherein the plurality of virtual spheres have centers that are non-collinear relative to the at least one tracking element.

6. The system as recited in claim 1, wherein the true intersection point and the symmetric intersection point are visualized on a display.

7. The system as recited in claim 1, wherein the at least two dimensions include three dimensions such that a three-dimensional image of the medical device is tracked in a two-dimensional image.

8. The system as recited in claim 1, wherein the three virtual elements are beamformed to prevent collinear origins for the times of flight of signals.

9. The system as recited in claim 1, wherein the system further comprises an imaging processor to generate a digital rendering of the position of the medical device in the visual image.

10. The system as recited in claim 1, wherein the plurality of virtual spheres include three spheres.

11. The system as recited in claim 10, wherein the three spheres are defined as:

$$r_1^2 = x^2 + y^2 + z^2$$

$$r_2^2 = (x-d)^2 + y^2 + z^2$$

$$r_3^2 = (x-i)^2 + (y-j)^2 + z^2$$

where x, y, and z are coordinates of a solution point, $r_1$ is a radius of the first sphere, $r_2$ is a radius of the second sphere, and $r_3$ is a radius of the third sphere.

12. A workstation, comprising:
an imaging probe having an array of transducers having transducer elements spaced apart from one another for exchanging energy with a tracked medical device in a subject, the array of transducers generating three virtual elements that are non-collinear with respect to the transducer elements;
a processor; and
memory coupled to the processor, the memory including trilateration instructions that when executed by the processor cause the processor to receive signals related to the tracked medical device inserted in the subject and computing times of flight of signals for a plurality of the transducer elements of the array of transducers relative to at least one tracking element on the tracked medical device and perform a trilateration procedure to yield a position of the tracked medical device within the subject by generating a plurality of virtual spheres that intersect at a true intersection point and a symmetric intersection point, and based on the times of flight of signals for the plurality of the transducer elements to determine a position of the at least one tracking element in at least two dimensions;
the memory further including an imaging processor that generates an image of the medical device and display the image of the medical device at the determined position in a visual image of the subject.

13. The workstation as recited in claim 12, wherein each of said virtual spheres emanates from one transducer element of the array of transducers and has a radius defined by a time of flight of signal for the transducer element that the virtual sphere emanates therefrom.

14. The workstation as recited in claim 12, wherein the plurality of virtual spheres have centers that are non-collinear relative to the at least one tracking element.

15. The workstation as recited in claim 12, wherein the true intersection point and the symmetric intersection point are visualized on a display.

16. The workstation as recited in claim 12, wherein the at least one virtual element is beamformed to prevent collinear origins for the times of flight of signals.

17. A method for imaging a medical device, comprising:
introducing a medical device into a subject, the medical device including at least one element for exchanging energy;
imaging the subject by an imaging device;
exchanging signals from a plurality of transducers arranged in an array with the at least one element, the plurality of transducers generating three virtual elements that are non-collinear with respect to the transducer elements;
determining times of flight of the signals between each of the plurality of transducers and the at least one element;
yielding a position of the medical device within the subject by generating a plurality of virtual spheres that intersect at a true intersection point and a symmetric intersection point; and
imaging the true intersection point by the imaging device to track a position of the medical device.

18. The method as recited in claim 17, further comprising beamforming a transmitted signal from one or more transducers to provide a new position for the three virtual elements.

* * * * *